United States Patent
Wu et al.

(10) Patent No.: US 12,097,001 B2
(45) Date of Patent: Sep. 24, 2024

(54) SYSTEMS AND METHODS FOR INSTRUMENT INSERTION CONTROL

(71) Applicant: INTUITIVE SURGICAL OPERATIONS, INC., Sunnyvale, CA (US)

(72) Inventors: Melody Wu, Sunnyvale, CA (US); Samuel Kwok Wai Au, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 778 days.

(21) Appl. No.: 17/236,874

(22) Filed: Apr. 21, 2021

(65) Prior Publication Data

US 2021/0236221 A1     Aug. 5, 2021

Related U.S. Application Data

(63) Continuation of application No. 16/084,449, filed as application No. PCT/US2017/018193 on Feb. 16, 2017, now Pat. No. 11,013,567.

(Continued)

(51) Int. Cl.
*A61B 34/35* (2016.01)
*A61B 34/00* (2016.01)
(Continued)

(52) U.S. Cl.
CPC ............. *A61B 34/35* (2016.02); *A61B 34/20* (2016.02); *A61B 34/37* (2016.02); *A61B 34/76* (2016.02);
(Continued)

(58) Field of Classification Search
CPC ......... A61B 34/35; A61B 34/20; A61B 34/37; A61B 34/76; A61B 90/00; A61B 34/70; A61B 2090/064
See application file for complete search history.

(56) References Cited

U.S. PATENT DOCUMENTS 6,331,191 B1    12/2001    Chobotov
6,377,011 B1    4/2002    Ben-Ur
(Continued)

FOREIGN PATENT DOCUMENTS

CN    101528151 A    9/2009
CN    102711635 A    10/2012
(Continued)

OTHER PUBLICATIONS

International Search Report and Written Opinion for Application No. PCT/US2017/018193, mailed on May 25, 2017, 9 pages.
(Continued)

*Primary Examiner* — Julian W Woo
(74) *Attorney, Agent, or Firm* — Artegis Law Group, LLP

(57) ABSTRACT

Techniques for instrument insertion control include a manipulator system. The manipulator system includes a manipulator configured to support an instrument and a control system coupled to the manipulator. The control system is configured to determine an insertion profile associated with at least one of the instrument or a cannula through which the instrument is configured to be inserted and resist or assist a manual insertion of the instrument through the cannula according to the insertion profile, wherein the resisting or assisting causes a velocity of the manual insertion to be uniform in response to a uniform force applied by the manual insertion.

20 Claims, 11 Drawing Sheets

Related U.S. Application Data

(60) Provisional application No. 62/309,609, filed on Mar. 17, 2016.

(51) Int. Cl.
  *A61B 34/20* (2016.01)
  *A61B 34/37* (2016.01)
  *A61B 90/00* (2016.01)
  *A61B 90/98* (2016.01)

(52) U.S. Cl.
  CPC .............. *A61B 90/00* (2016.02); *A61B 90/06* (2016.02); *A61B 90/98* (2016.02); *A61B 2090/064* (2016.02)

(56) References Cited

U.S. PATENT DOCUMENTS

| | | | |
|---|---|---|---|
| 6,491,701 | B2 | 12/2002 | Tierney et al. |
| 6,817,974 | B2 | 11/2004 | Cooper et al. |
| 7,689,320 | B2 | 3/2010 | Prisco et al. |
| 8,551,115 | B2 | 10/2013 | Steger et al. |
| 9,060,678 | B2 | 6/2015 | Larkin et al. |
| 9,089,351 | B2 | 7/2015 | Park et al. |
| 9,138,284 | B2 | 9/2015 | Krom et al. |
| 11,013,567 | B2 | 5/2021 | Wu et al. |
| 11,039,891 | B2 * | 6/2021 | Shochat ............... A61B 5/6848 |
| 11,534,079 | B2 * | 12/2022 | Page ....................... A61B 5/065 |
| 11,596,486 | B2 * | 3/2023 | Rabindran ............. A61B 34/77 |
| 11,911,910 | B2 * | 2/2024 | Gonenc .................. A61B 34/35 |
| 2010/0036245 | A1 | 2/2010 | Yu et al. |
| 2010/0114288 | A1 | 5/2010 | Haller et al. |
| 2010/0286711 | A1 | 11/2010 | Doyle |
| 2011/0071541 | A1 | 3/2011 | Prisco et al. |
| 2011/0071542 | A1 | 3/2011 | Prisco et al. |
| 2011/0071543 | A1 | 3/2011 | Prisco et al. |
| 2011/0178508 | A1 | 7/2011 | Ullrich |
| 2011/0245805 | A1 | 10/2011 | Swinehart et al. |
| 2013/0012930 | A1 | 1/2013 | Ruiz et al. |
| 2013/0211423 | A1 | 8/2013 | Blumenkranz et al. |
| 2014/0052298 | A1 | 2/2014 | Hourtash et al. |
| 2014/0128849 | A1 | 5/2014 | Au et al. |
| 2015/0045814 | A1 | 2/2015 | Prisco et al. |
| 2015/0057575 | A1 | 2/2015 | Tsusaka et al. |
| 2015/0164598 | A1 | 6/2015 | Blumenkranz et al. |
| 2015/0297864 | A1 | 10/2015 | Kokish et al. |
| 2016/0030118 | A1 | 2/2016 | Devengenzo et al. |

FOREIGN PATENT DOCUMENTS

| | | |
|---|---|---|
| CN | 103402574 A | 11/2013 |
| CN | 104042259 A | 9/2014 |
| JP | 2013517065 A | 5/2013 |
| JP | 2015024033 A | 2/2015 |
| WO | WO-2011037718 A1 | 3/2011 |
| WO | WO-2011088357 A1 | 7/2011 |
| WO | WO-2011126877 A1 | 10/2011 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Office Action for Chinese Application No. CN202110751816.8, mailed Jan. 6, 2024, 20 pages.

* cited by examiner

SYSTEMS AND METHODS FOR INSTRUMENT INSERTION CONTROL

CROSS-REFERENCES TO RELATED APPLICATIONS

This patent application is a continuation of U.S. patent application Ser. No. 16/084,449, filed Sep. 12, 2018, issued as U.S. Pat. No. 11,013,567, which is the U.S. National Stage patent application of International Patent Application No. PCT/US2017/018193, filed Feb. 16, 2017 which designated the U.S. and claims priority to and the benefit of the filing date of U.S. Provisional Patent Application 62/309,609, entitled "SYSTEMS AND METHODS FOR INSERTION RESISTANCE MODULATION DURING INSTRUMENT INSERTION" filed Mar. 17, 2016, each of which is incorporated by reference herein in its entirety.

TECHNICAL FIELD

The present disclosure is directed to medical systems such as surgical systems, and methods for use in medical operations including minimally invasive surgery and teleoperational surgery. The present disclosure discusses systems and methods for modulating or otherwise controlling the insertion force associated with manual instrument insertion.

BACKGROUND

Minimally invasive medical techniques are intended to reduce the amount of extraneous tissue that is damaged during diagnostic or surgical procedures, thereby reducing patient recovery time, discomfort, and harmful side effects. Minimally invasive telesurgical systems have been developed to increase a surgeon's dexterity and to avoid some of the limitations on traditional minimally invasive techniques. In telesurgery, the surgeon uses some form of remote control, e.g., a servomechanism or the like, to manipulate surgical instrument movements, rather than directly holding and moving the instruments by hand. In robotically assisted telesurgery, the surgeon typically operates a master controller to control the motion of surgical instruments at the surgical site from a location that may be remote from the patient (e.g., across the operating room, in a different room, or a completely different building from the patient). Before the start of the telesurgery, the surgical instruments (including an endoscope) are installed on a surgical manipulator and then introduced under the manual control of physicians into an open surgical site or more typically through cannulas into a body cavity. During this process, the surgical manipulator enters into a control mode that is designed to facilitate and assist smooth and safe manual instrument introduction by physicians. This mode may be selected via the master controller or may be automatically selected as part of a predetermined workflow.

For minimally invasive surgical procedures, the surgical instruments, controlled by the surgical manipulator, may be introduced into the body cavity through various types of cannula components, including cannulas, depending on the instruments to be inserted and the type of procedure to be performed. The force required to insert a particular surgical instrument through a particular cannula component may depend upon qualities such as materials and geometry of the cannula component. For example, inserting a straight-but-bendable surgical instrument through a curved cannula may require a significantly greater amount of force as compared to inserting the same surgical instrument through a straight cannula. Further, a single cannula can often contain various geometric properties along its length, which can include straight and curved portions or a various combination of linear and nonlinear portions.

Inserting an instrument (such as a flexible instrument) through such a curved cannula can require a non-uniform amount of force, making it difficult for the user (such as a surgeon or other operating room staff) to manage the instrument insertion process smoothly. Also, inserting different instruments with different diameters through a cannula component comprising a cannula seal can require different amounts of insertion force, making it potentially disconcerting difficult for the operator to manage the instrument insertion process across different instruments. Failure to manage the process smoothly can cause an abrupt change in velocity, which can lead to cannula component damage (e.g., internal scraping), instrument buckling, instrument overshooting the desired instrument tip location, user dissatisfaction, and the like. Improved systems and methods are needed for mounting and controlling these surgical instruments during insertion through various cannulas to provide a more uniform feel to the user.

SUMMARY

The embodiments of the invention are summarized by the claims that follow below.

In one embodiment, a teleoperational surgical system comprises a manipulator and a control system communicatively coupled with the manipulator. The manipulator is configured to be operatively coupled to a medical instrument. The manipulator is also adapted to move the medical instrument through a cannula component. The control system is operative to determine an insertion profile associated with at least one of the medical instrument and the cannula component. The control system is configured to control an insertion force in accordance with the insertion profile and affect motion of the medical instrument during manual insertion of the medical instrument through the cannula component.

In one embodiment, a control system is provided. The control system may include a memory storing a plurality of damping profiles and executable instructions and a processor configured to execute the executable instructions stored in the memory. Executing the instructions may cause the processor to identify a cannula, through which a medical instrument is to be inserted, as being associated with a type of the cannula, determine a position of the medical instrument being inserted through the cannula, an apply a corresponding damping profile from the plurality of damping profiles to impede the movement of the medical instrument as the medical instrument is inserted through the cannula.

In another embodiment, a method of controlling a teleoperational surgical system during insertion of a medical instrument through a cannula component is provided. The method comprises identifying at least one element type, retrieving from memory an insertion profile associated with the at least one component type, determining a location of the medical instrument relative to the cannula component, and applying an impeding or assistive force to the medical instrument based on the insertion profile as the medical instrument is inserted through the cannula component. The element type is an instrument type of the medical instrument, or a cannula component type of the cannula component.

In yet another embodiment, a method of controlling a teleoperational surgical system during insertion of a medical instrument is provided. Such a method may include identifying a cannula type of a cannula through which the medical instrument is to be inserted, retrieving a profile associated with the cannula type of the cannula, determining a location of a distal tip of the medical instrument relative to the cannula, and applying a force to the medical instrument based on the profile associated with the cannula type of the cannula.

In one embodiment, a system that is able to modulate an insertion resistance force (also called "insertion resistive force" or "resistive force") when inserting a medical instrument through a cannula is provided. Such a system may include a control system in communicatively coupled with a moveable input device and a manipulator configured to be operatively coupled to a flexible medical instrument. The flexible medical instrument comprises a proximal end, a distal end, and a flexible portion between the proximal and distal ends. The manipulator is adapted to move the flexible medical instrument through a cannula. The control system is operative to identify the cannula and determine a damping profile associated with the cannula. And the control system is configured to apply the damping profile to modulate a resistive insertion force to impede the motion of the medical instrument during manual insertion through the cannula.

These embodiments and others may be better understood by reference to the accompanying drawings and detailed description.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

These figures may be better understood by reference to the following detailed description.

DETAILED DESCRIPTION

In the following detailed description of the embodiments of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

This detailed description discloses systems and methods for controlling surgical instruments during insertion through various cannulas or other cannula components (or combinations of various cannulas and cannula components) to provide a uniform feel to the surgeon or other operator inserting the instruments. Through modulating or otherwise controlling the insertion force associated with instrument insertion, the systems and methods facilitate instrument insertion such that the surgeon or other operator can manage the insertion smoothly. This reduces the likelihood of damaging the cannula, other cannula components, instruments, tissue, or combination thereof.

Figure 1:
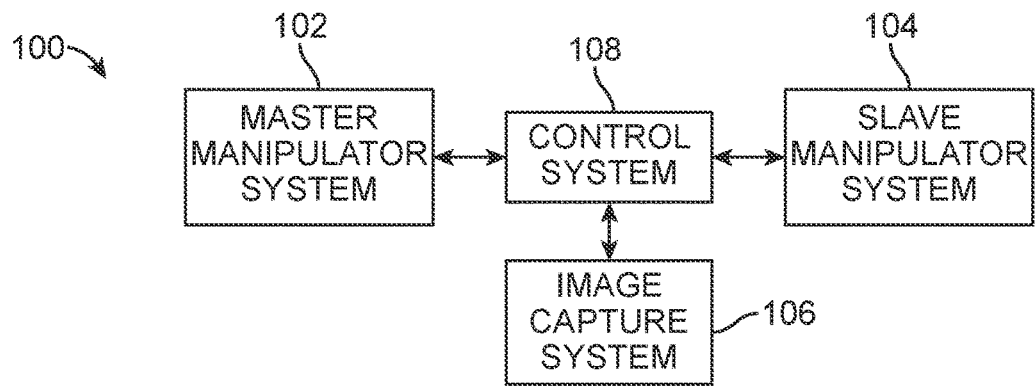
FIG. 1 is a schematic depiction of a teleoperational surgical system according to an embodiment of the present disclosure.

Referring to FIG. 1 of the drawings, an exemplary teleoperational surgical system 100 is illustrated therein. The teleoperational surgical system 100 includes a master manipulator system 102, also referred to as a master console 102 or surgeon's console 102 when the master manipulator is contained within such a console (see, FIG. 3). The master manipulator system 102 is configured for inputting a surgical procedure and a slave manipulator system 104. The slave manipulator system 104 is also referred to as a patient-side manipulator (PSM) system, for the teleoperational movement of surgical instruments at a surgical site within a patient. "Surgical instrument" is used herein to indicate medical instruments that may be inserted through a cannula during a medical procedure such as diagnostic procedures and surgical procedures. Thus, types of surgical instruments include various tissue manipulation tools such as various ones designed for dissecting, stapling, cauterizing, grasping, and other forms or combinations of tissue manipulation. Other example types of instruments include those designed for a function other than tissue manipulation, such as various instrument types used for optical, ultrasonic, RF, fluoroscopic, or other imaging, retrieving specimens, etc. Instrument can also vary in geometry, material, and mechanical properties such as flexibility. For example, some instruments are designed to be flexible and readily bend to conform to curved insertion channels such as those provided by curved cannulas. As another example, some instruments are designed to stiff, and do not readily bend or conform to curved insertion channels.

The teleoperational surgical system 100 is used to perform minimally invasive teleoperational surgery. One example of a teleoperational surgical system that can be used to implement the systems and techniques described in this disclosure is a da Vinci® Surgical System manufactured by Intuitive Surgical, Inc. of Sunnyvale, California. In one embodiment the slave manipulator system 104 may be free-standing (see, FIG. 2). In an alternative embodiment, the slave manipulator system 104 may be mounted to other equipment in the surgical arena, including, for example, a surgical bed. In still another alternative embodiment, the slave manipulator system 104 may include both free-standing and bed-mounted components.

The teleoperational surgical system 100 also includes an image capture system 106 which includes an image capture device, such as an endoscope, and related image processing hardware and software. The teleoperational surgical system 100 also includes a control system 108 that is operatively linked to sensors, motors, actuators, and other components of the manipulator systems 102, 104 and to the image capture system 106. In some embodiments, the control system 108 may be integrated into one of the manipulator systems 102 and 104. In other embodiments, the control system 108 may be provided in a separate housing and coupled to the manipulator systems 102 and 104 via one or more communication links. A more detailed embodiment of the control system 108 may be understood by reference to FIG. 9.

The surgical system 100 is used by a system operator, generally a surgeon, who performs a minimally invasive surgical procedure on a patient. The system operator sees images, captured by the image capture system 106, presented for viewing at the master console 102. In response to the surgeon's input commands, the control system 108 effects servomechanical movement of surgical instruments coupled to the teleoperational slave manipulator system 104.

The control system 108 includes at least one processor and typically a plurality of processors for effecting control between the master manipulator system 102, the slave manipulator system 104, and the image capture system 106. The control system 108 also includes software programming instructions to implement some or all of the methods described herein. While control system 108 is shown as a single block in the simplified schematic of FIG. 1, the system may comprise a number of data processing circuits (e.g., on the surgeon's console 102 and/or on the slave manipulator system 104), with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the teleoperational systems described herein.

Figure 2:
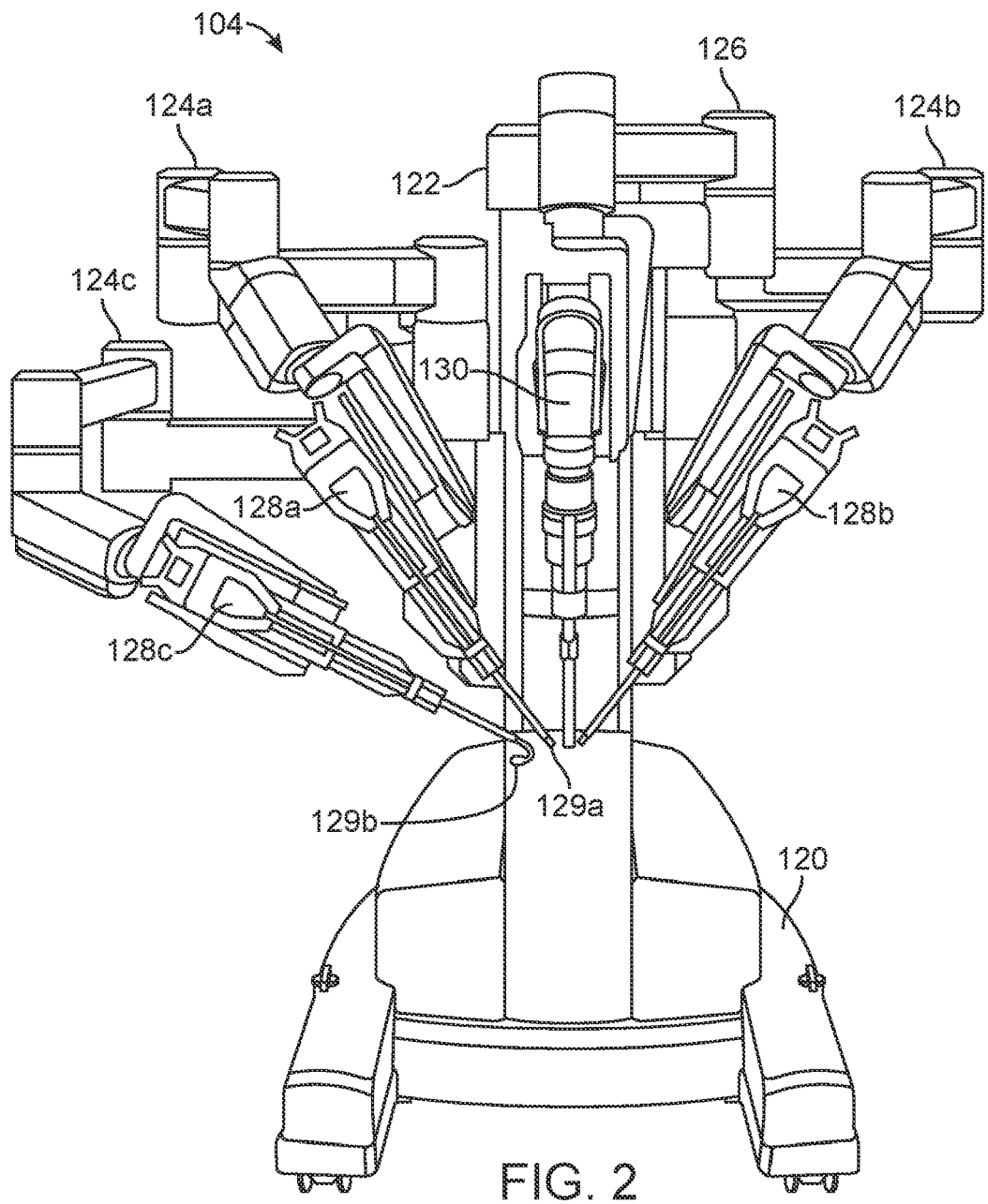
FIG. 2 is a front elevation view of the patient side cart including three patient side manipulators and one endoscopic manipulator according to one embodiment of the disclosure.

FIG. 2 is a front elevation view of the patient-side manipulator 104 according to one embodiment of the teleoperational surgical system 100. The patient-side manipulator 104 includes a base 120 that rests on the floor, a support tower 122 that is mounted on the base 120, and several arms that support surgical tools (including portions of the image capture system 106). As shown in FIG. 2, arms 124a, 124b are instrument arms that support and move the surgical instruments used to manipulate tissue, and arm 126 is a camera arm that supports and moves the endoscope. FIG. 2 also shows an optional third instrument arm 124c that is supported on the back side of support tower 122 and that can be positioned to either the left or right side of the patient-side manipulator as necessary to conduct a surgical procedure. FIG. 2 further shows interchangeable surgical instruments 128a, 128b, 128c mounted on the instrument arms 124a, 124b, 124c, respectively, and it shows endoscope 130 mounted on the camera arm 126. Knowledgeable persons will appreciate that the arms that support the instruments and the camera may also be supported by a base platform (fixed or moveable) mounted to a ceiling or wall, or in some instances to another piece of equipment in the operating room (e.g., the operating table). Likewise, they will appreciate that two or more separate bases may be used (e.g., one base supporting each arm). The surgical instruments 128a, 128b include end effectors 129a, 129b, respectively.

Figure 3:
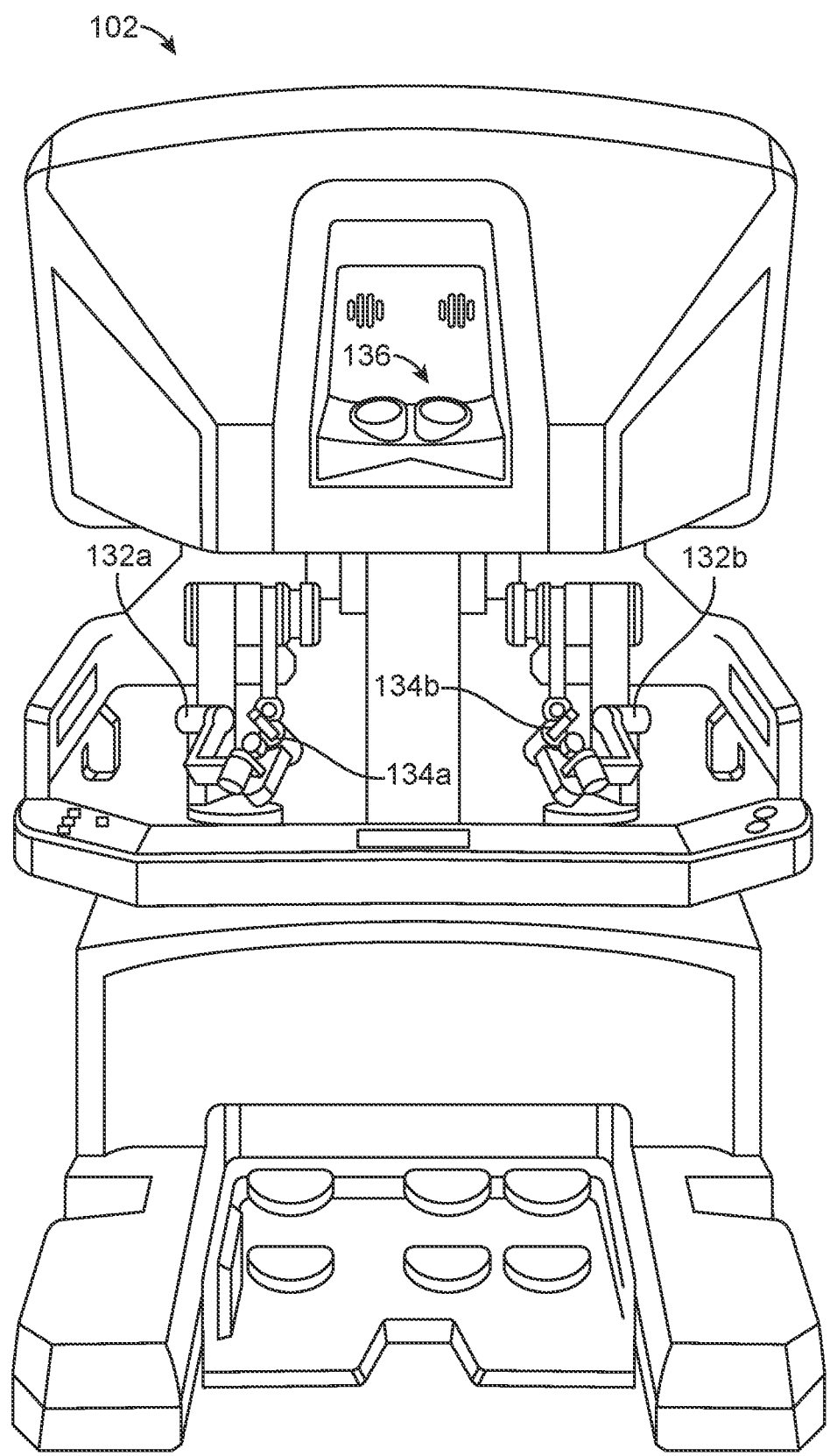
FIG. 3 is a front elevation view of a surgeon's console in a teleoperational surgical system according to one embodiment of the disclosure.

FIG. 3 is a front elevation view of a master console 102 component according to one embodiment of the teleoperational surgical system 100. The master console 102 may be equipped with left and right multiple degree of freedom (DOF) master tool manipulators (MTM's) 132a, 132b, which are kinematic chains that are used to control the surgical tools (which include the endoscope and various cannulas). The MTM's 132 may be referred to simply as "master," and their associated arms 124 and surgical instruments 128 may be referred to simply as "slave." The surgeon grasps a pincher assembly 134a, 134b on each MTM 132, typically with the thumb and forefinger, and can move the pincher assembly to various positions and orientations. Each MTM 132a, 132b will generally allow movement within the master workspace with a plurality of degrees of freedom, typically with six degrees of freedom, three rotational degrees of freedom and three translational degrees of freedom.

When a tool control mode is selected, each MTM 132 is coupled to control a corresponding instrument arm 124 for the patient-side manipulator 104. For example, left MTM 132a may be coupled to control instrument arm 124a and instrument 128a, and right MTM 132b may be coupled to control instrument arm 124b and instrument 128b. If the third instrument arm 124c is used during a surgical procedure and is positioned on the left side, then left MTM 132a can be switched between controlling arm 124a and instrument 128a to controlling arm 124c and instrument 128c. Likewise, if the third instrument arm 124c is used during a surgical procedure and is positioned on the right side, then right MTM 132a can be switched between controlling arm 124b and instrument 128b to controlling arm 124c and instrument 128c. In alternative embodiments, the third instrument arm may be controlled by either the left or right MTM to accommodate surgical convenience. In some instances, control assignments between MTM's 132a, 132b and arm 124a/instrument 128a combination and arm 124b/instrument 128b combination may also be exchanged. This may be done, for example, if the endoscope is rolled 180 degrees, so that the instrument moving in the endoscope's field of view appears to be on the same side as the MTM the surgeon is moving.

Surgeon's console 102 also includes a stereoscopic image display system 136. Left side and right side images captured by the stereoscopic endoscope 130 are output on corresponding left and right displays, which the surgeon perceives as a three-dimensional image on display system 136. In one configuration, the MTM's 132 are positioned below display system 136 so that the images of the surgical tools shown in the display appear to be co-located with the surgeon's hands below the display. This feature allows the surgeon to intuitively control the various surgical tools in the three-dimensional display as if watching the hands directly.

Accordingly, the MTM servo control of the associated instrument arm and instrument is based on the endoscopic image reference frame.

The endoscopic image reference frame is also used if the MTM's are switched to a camera control mode. For example, if the camera control mode is selected, the surgeon may move the distal end of the endoscope by moving one or both of the MTM's together (portions of the two MTM's may be servo-mechanically coupled so that the two MTM portions appear to move together as a unit). The surgeon may then intuitively move (e.g., pan, tilt, zoom) the displayed stereoscopic image by moving the MTM's as if holding the image in the hands.

The surgeon's console 102 is typically located in the same operating room as the patient-side manipulator 104, although it is positioned so that the surgeon operating the console is outside the sterile field. One or more assistants typically assist the surgeon by working within the sterile surgical field (e.g., to change tools on the patient side cart, to perform manual retraction, etc.). Accordingly, the surgeon operates remote from the sterile field, and so the console may be located in a separate room or building from the operating room. In some implementations, two surgeon's consoles 102 (either co-located or remote from one another) may be networked together so that two surgeons can simultaneously view and control tools at the surgical site.

Figure 4:
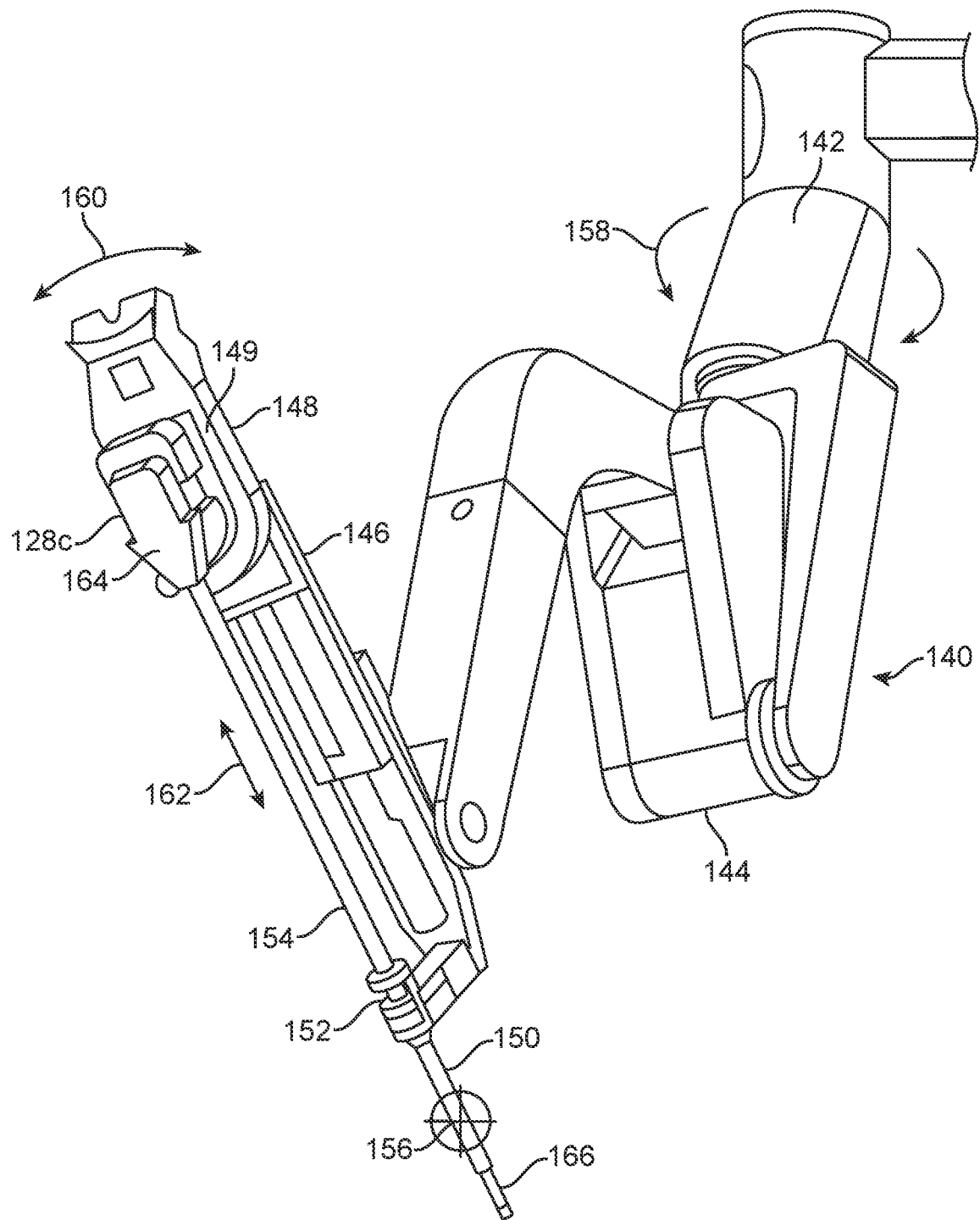
FIG. 4 is a perspective view of a patient side manipulator arm with a mounted surgical instrument according to one embodiment of the disclosure.

FIG. 4 is a perspective view of a manipulator portion 140 of the control arm 124c with the mounted surgical instrument 128c. Sterile drapes and associated mechanisms that are normally used during surgery are omitted for clarity. The manipulator 140 includes a yaw actuator 142, a pitch actuator 144, and an insertion and withdrawal ("I/O") actuator 146. The surgical instrument 128c is shown mounted at an instrument spar 148 including a mounting carriage 149. An illustrative straight cannula 150 is shown mounted to cannula mount 152. Other types of cannulas may be used, as is discussed in more detail below. Shaft 154 of instrument 128c extends through cannula 150. Manipulator 140 is mechanically constrained so that it moves instrument 128c around a stationary remote center of motion 156 (also "remote center 156") located along the instrument shaft. Yaw actuator 142 provides yaw motion 158 around remote center 156, pitch actuator 144 provides pitch motion 160 around remote center 156, and I/O actuator 146 provides insertion and withdrawal motion 162 through remote center 156. The manipulator 140 may include an encoder to track position and velocity along the insertion axis of the I/O actuator 146. Typically the remote center 156 is locked at the incision in the patient's body wall during surgery and to allow for sufficient yaw and pitch motion to be available to carry out the intended surgical task. Alternatively, the remote center of motion may be located outside of the body to allow a greater range of motion without contacting the patient. Knowledgeable persons will understand that motion around a remote center of motion may be constrained by the use of software or by a physical constraint defined by a mechanical assembly.

Matching force transmission disks in mounting carriage 149 and instrument force transmission assembly 164 couple actuation forces from actuators in manipulator 140 to move various parts of instrument 128c in order to position and orient a tissue probe 166 mounted at the distal end of the curved shaft 154. Such actuation forces may typically roll instrument shaft 154 (thus providing another DOF through the remote center 156). Embodiments of force transmission assemblies are provided in U.S. Pat. No. 6,331,191 (filed Oct. 15, 1999; disclosing "Surgical Robotic Tools, Data Architecture, and Use") and U.S. Pat. No. 6,491,701 (filed Jan. 12, 2001; disclosing "Mechanical Actuator Interface System for Robotic Surgical Tools") which are incorporated herein by reference in its entirety. In alternative embodiments, the instrument 128c may include a wrist at the distal end of the shaft that provides additional yaw and pitch DOF's. The tissue probe 166 may be, for example, a general tissue manipulator, a tissue elevator, or a tissue retractor. In alternative embodiments, the instrument 128c may include an imaging component.

Figure 5:
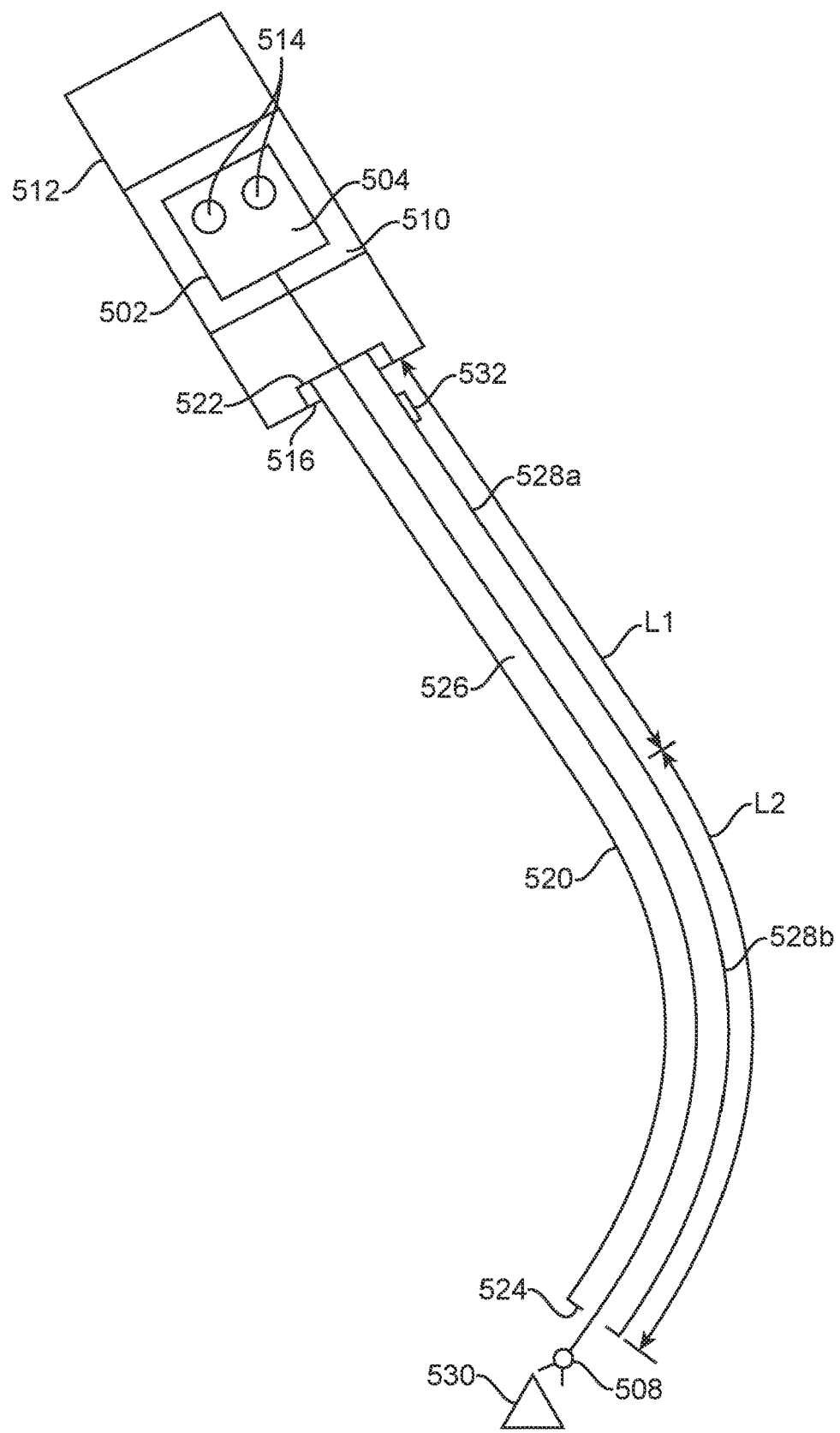
FIGS. 5 and 6 are diagrammatic views that show an instrument shaft running through extending from various cannula configurations.

FIG. 5 is a schematic view of a portion of an example patient side robotic manipulator that supports and moves a combination of a curved cannula and a passively flexible surgical instrument. As depicted in FIG. 5, a telerobotically operated surgical instrument 502 includes a force transmission mechanism 504, a flexible instrument shaft 506, and an end effector 508. In this example, the force transmission mechanism 504 is located at a proximal end of the medical instrument configured to extend proximally from the cannula after the medical instrument is moved through the cannula, the end effector 508 is located at a distal end of the medical instrument configured to extend distally from the cannula after the medical instrument is moved through the cannula, and the flexible instrument shaft 506 is a flexible portion between the proximal and distal ends. Instrument 502 is an example medical instrument designed for surgical procedures. Other example medical instruments include various imagers and other tools that may be inserted through a cannula during a medical procedure. Instrument 502 is mounted on an instrument carriage 510 (like the carriage 149 of FIG. 4) of a manipulator 512 (like the manipulator 140 of FIG. 4). Previously described components are schematically depicted for clarity. Interface discs 514 couple actuation forces from servo actuators in manipulator 512 to move instrument 502 components. End effector 508 illustratively operates with a single DOF (e.g., closing jaws). A wrist to provide one or more end effector DOFs (e.g., pitch, yaw; see e.g., U.S. Pat. No. 6,817,974 (filed Jun. 28, 2002) (disclosing surgical tool having positively positionable tendon-actuated multi-disk wrist joint), which is incorporated herein by reference) is optional and is not shown. Many instrument implementations do not include such a wrist. Omitting the wrist simplifies the number of actuation force interfaces between manipulator 512 and instrument 502, and the omission also reduces the number of force transmission elements (and hence, instrument complexity and dimensions) that would be necessary between the proximal force transmission mechanism 504 and the distally actuated piece.

FIG. 5 further shows a curved cannula 520, which has a proximal end 522, a distal end 524, and a central channel 526 that extends between proximal end 522 and distal end 524. Curved cannula 520 is an example cannula component. Cannula components comprise the components which physically form the cannel through which a medical instrument may be inserted through during a medical procedure. Other example types of cannula components include cannula seals of various geometries, materials, and sizes that may be placed proximal to a cannula to provide a physical seal, and cannula reducers of various geometries, materials, and sizes that may be inserted into a cannula to reduce the inner diameter of the channel available to the medical instrument.

Curved cannula 520 is also an example cannula type comprising a linear section and a curved (nonlinear) section. Other example cannula types include straight cannulas, cannulas with multiple non-parallel linear sections, cannulas with multiple curved sections having different curvatures, cannulas with other combinations of linear and nonlinear sections, cannulas with different internal or external diameters, cannulas with different materials, multi-piece cannulas that are assembled for medical procedures, etc.

Curved cannula 520 is, in one implementation, a rigid, single piece cannula. As depicted in FIG. 5, proximal end 522 of curved cannula 520 is mounted on the manipulator 512's cannula mount 516. During initial instrument deployment, a user advances the instrument through the curved cannula 520 by manually applying force onto carriage 510 of manipulator 512 along the insertion axis. The force can be applied directly to the carriage 510 or the instrument 502. Instrument 502's flexible shaft 506 is passed through curved cannula 520's central channel 526 so that a distal portion of flexible shaft 506 and end effector 508 extend beyond cannula 520's distal end 524 in order to reach surgical site 530. During telesurgery, manipulator 512's I/O actuation, provided by the carriage 510, inserts and withdraws the flexible shaft 506 of instrument 502 through cannula 520 to move end effector 508 in and out.

In the above-described embodiments, the cannulas and the instrument shafts may be formed of rigid materials such as stainless steel or glass-epoxy composite. Alternatively, they may be formed of flexible materials such as a high modulus of elasticity plastic like Polyether ether ketone (PEEK), glass or carbon filled Polyether ether ketone (PEEK), or a glass-fiber-epoxy or a carbon-fiber-epoxy composite construction. The inside and outside diameters and physical construction of the shaft or cannula are chosen uniquely for each material choice to limit the magnitude of forces that can be applied to the body during use or allow the structure to bend sufficiently to follow a curved guide path within the instrument or cannula during use. Additional information about the cannulas and instrument shafts, including information about material composition and flexibility, is provided in detail in U.S. patent application Ser. No. 12/618,608 (filed Nov. 13, 2009; disclosing "Curved Cannula Instrument") which is incorporated herein by reference, in its entirety.

In some embodiments, a tag 532 may be secured to or embedded within a mounting fitting at the proximal end 522. The tag 532 may be a radiofrequency identification (RFID) tag. Other embodiments may include another machine-readable tag, such as a magnetic tag having a binary pattern. The machine-readable tag 532 may be read via a wireless communication or may be a visible machine-readable tag such as a QR code or a barcode that may be scanned preoperatively. By reading the tag 532, the surgical system 100 may identify a type of the cannula 520 from a cannula database. Identifying the type of the cannula 520 may retrieve from memory geometric information characterizing the cannula 520. For example, by identifying the type of the cannula 520, lengths and diameters of the first portion 528a and the second portion 528b may be accessed by a processing device of the control system 108. In some embodiments, an operator of the surgical system 100 may manually select a type of the cannula to be used during a procedure prior to beginning that procedure.

Due to the differences in flexibility, geometry, and materials of the instruments and cannulas that may be used with the surgical system 100, the forces required by the user to move a given instrument through a given cannula may be substantially different from the forces required to move a different instrument through a different cannula or to move the same instrument through different cannulas. Additionally, the force required by the user to move a given instrument through a given cannula may change substantially while the instrument is being inserted through the cannula. The cannula 520 includes a first portion 528a that is straight and a second portion 528b that is curved. While the distal tip of the flexible shaft 506 is forced through the first portion 528a by the user, a first amount of force may be needed to move the distal tip at a desired velocity. When the distal tip of the flexible shaft 506 is passing through the second portion 528b, the distal tip of the flexible shaft 506 may interact with the interior wall of the second portion 528b such that a second amount of force may be needed to move the distal tip at the desired velocity. The second amount of force may be greater than the first amount of force. Because of that, the user may insert the instrument faster in the first portion 528a and may slow down abruptly when transitioning from portions 528a to 528b, which may potentially create damage in the cannula interior wall and may also cause instrument buckling. And when the instrument exists the cannula, transitioning from portion 528b to 528c, the user may have a tendency to insert the instrument faster than through portion 528b, and potentially overshoot the target tip position and unintentionally impale tissue. As provided herein, the control system 108 may be configured to adjust an amount of compensating resistive force (i.e., a damping force) provided by the manipulator 512 through the carriage 510 such that throughout the entire manual insertion process, so that the velocity of the distal tip of the cannula 520 remains constant along the length of the cannula 520 and as the distal tip of the flexible shaft 506 exits the cannula 520. Also as provided herein, the control system 108 may be configured to adjust an amount of compensating assistive force (i.e., a negative damping force or an assistive force) provided by the manipulator 512 through the carriage 510 to achieve the same. Thus, various embodiment of the control system 108 may be configured to control an insertion force in accordance with an insertion profile to increase a spatial uniformity of a manual insertion force to be exerted to manually insert the medical instrument through the cannula component. The control of the insertion force may be accomplished by modulating an amount of compensating resistive force, modulating an amount of compensating assistive force, or modulating both an amount of compensating resistive force and an amount of compensating assistive force. For example, the control system 108 may be configured to provide resistive force for a first instrument location relative to the cannula component, and assistive force for a second instrument location relative to the cannula component that is different instrument location.

The materials, diameters, and lengths of the types of instruments and cannula components (including cannulas) that may be used with the surgical system 100 may be stored in one or more databases of the control system 108. For example, a length L1 of the first portion 528a and a length L2 of the second portion 528b may be stored in a database along with other information, such as information characterizing the curvature of the curved portion 528b. From this information, the control system 108 may calculate the different amounts of force required to move different flexible instruments through different portions of different cannulas and the different amounts of modulating or compensating force that should be applied to resist the motion of different flexible instruments through different portions of different cannulas in response to the user's velocity during manual instrument insertion in order to prevent damage to the cannulas or the medical instruments and to prevent sudden movement of the instrument.

Figure 6:
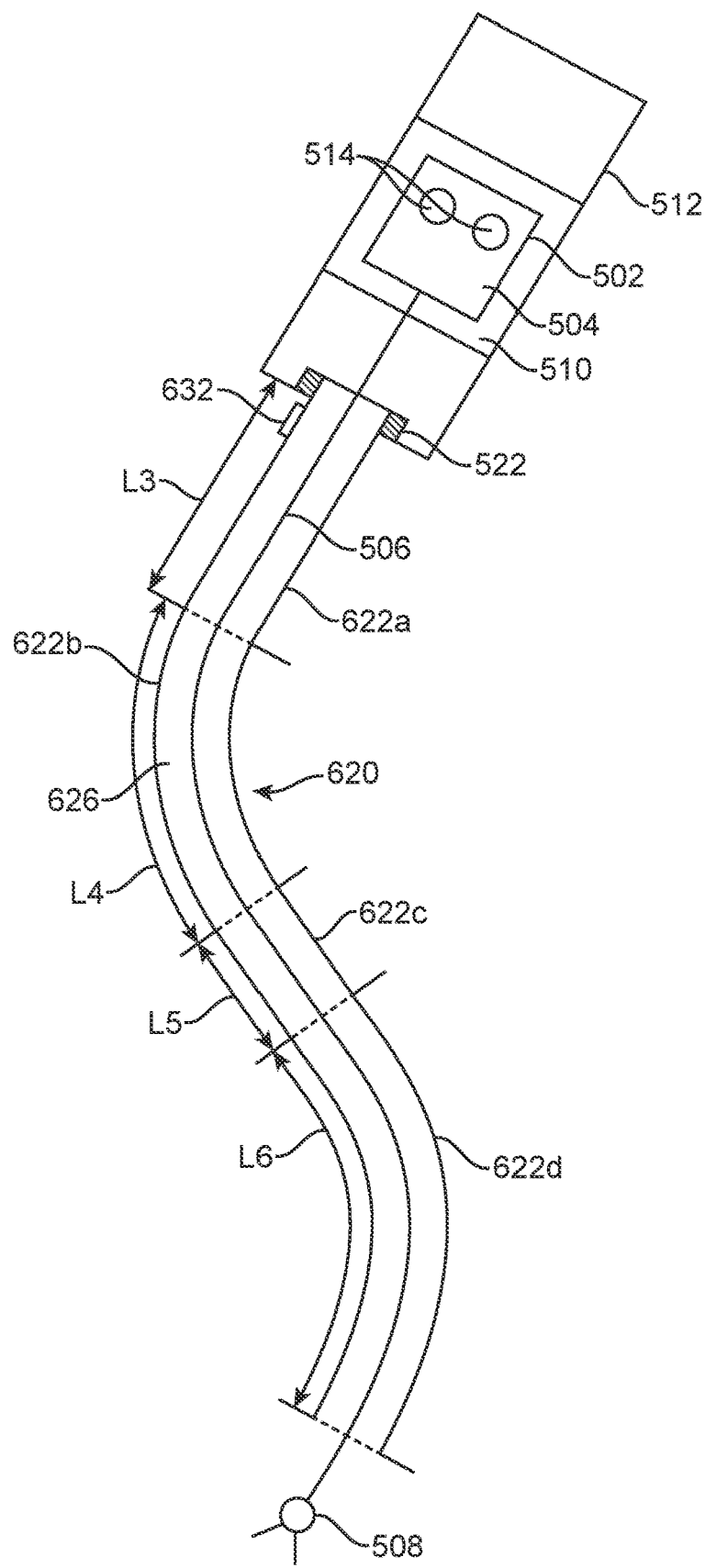

FIG. 6 is a schematic view of a portion of an example patient side robotic manipulator that supports and moves a combination of another implementation of a curved cannula and a passively flexible surgical instrument. Like FIG. 5, FIG. 6 shows the telerobotically operated surgical instrument 502 including the force transmission mechanism 504, the flexible instrument shaft 506, and the end effector 508. Instrument 502 is mounted on the instrument carriage 510 (like the carriage 149 of FIG. 4) of the manipulator 512 (like the manipulator 140 of FIG. 4).

The flexible instrument 506 is shown as having its distal tip exiting a cannula 620. The cannula 620 includes multiple curves. The length of the cannula 620 may be divided into four portions a first straight portion 622a having a length L3, a first curved portion 622b having a length L4, a second straight portion 622c having a length L5, and a second curved portion 622d having a length L6. During the initial manual insertion, in which there is no active force applied by the manipulator 512 through the carriage 510, while moving the distal tip of the flexible shaft 506 through the channel 626, a first amount of resistive force may be perceived by the user while the distal tip is within the first portion 622a, a second amount of resistive force may be perceived by the user while the distal tip is within the second portion 622b, a third amount of resistive force may be perceived by the user while the distal tip is within the third portion 622c, and a fourth amount of resistive force may be perceived by the user while the distal tip is within the fourth portion 622d. Additionally, a fifth amount of resistive force may be perceived by the user after the distal tip passes beyond the fourth portion 622d. The first, second, third, fourth, and fifth amounts of resistive force may be different from each other and may also depend on the velocity at which the user moves the carriage 510 along. Those amounts of force may define an insertion force profile and may be used in a resistive force modulation strategy that is associated with the cannula type that identifies the cannula 620.

Figure 7A:
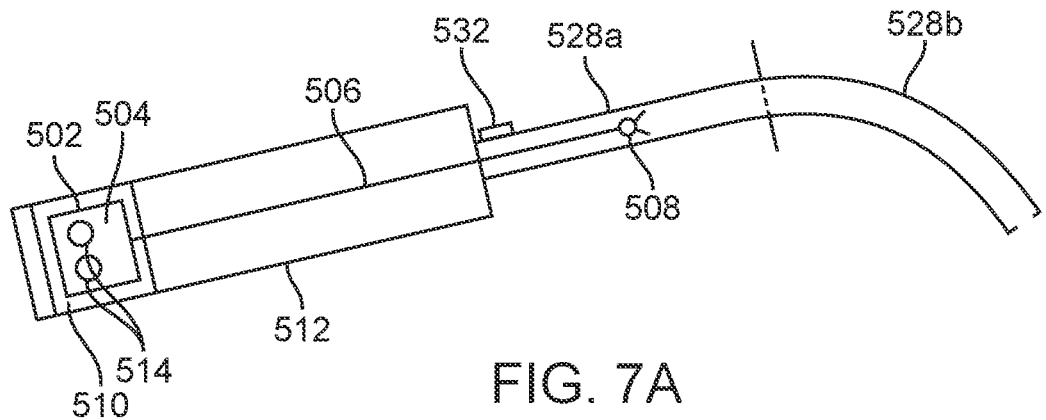
FIGS. 7A, 7B, and 7C are a series of diagrammatic views showing an instrument shaft as it extends through the cannula configuration of FIG. 5.
Figure 7B:
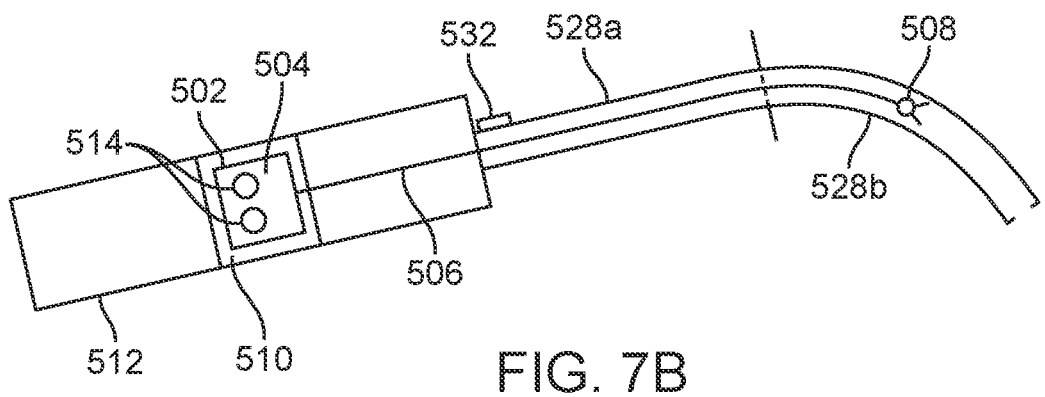
Figure 7C:
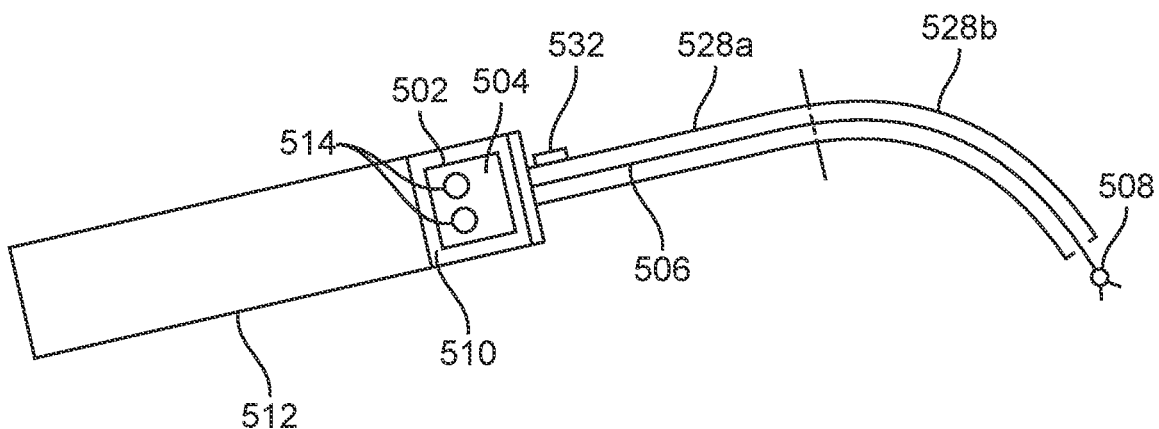

FIGS. 7A, 7B, and 7C are a series of diagrammatic views showing an instrument shaft as it extends through the cannula configuration of FIG. 5. FIG. 7A shows the distal tip of the flexible instrument shaft present within the first portion 528a of the cannula 520. FIG. 7B shows the distal tip of the flexible instrument shaft present within the second portion 528b of the cannula 520. Because the second portion 528b is curved, a greater amount of force may be applied by the user to push the distal tip of the flexible instrument shaft along the length L2 of the curved portion 528b, at a given velocity, than is required to push the distal tip along the length L1 of the straight portion 528a. FIG. 7C shows the distal tip of the flexible instrument shaft as having exited the cannula 520. Upon exiting the cannula 520, a force required to push the flexible instrument shaft through the cannula 520 may decrease.

Figure 8A:
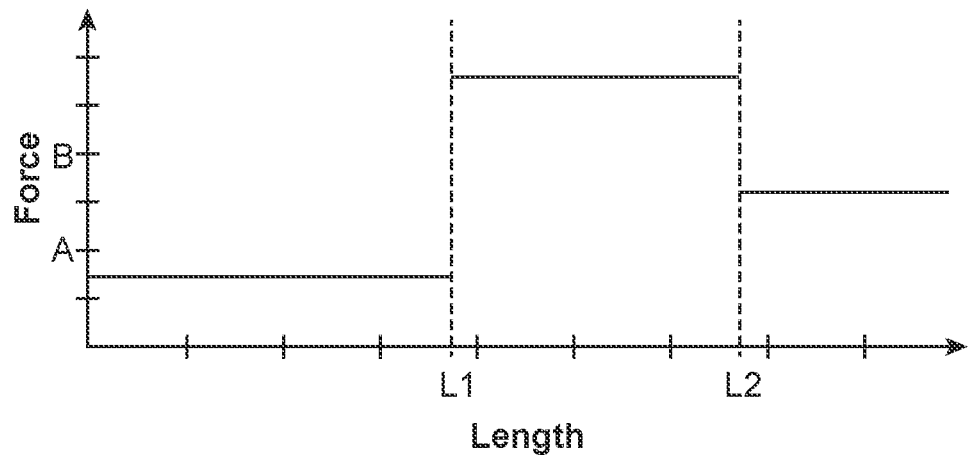
FIGS. 8A and 8B are plots relating an insertion force to an insertion length for various cannula configurations.
Figure 8B:
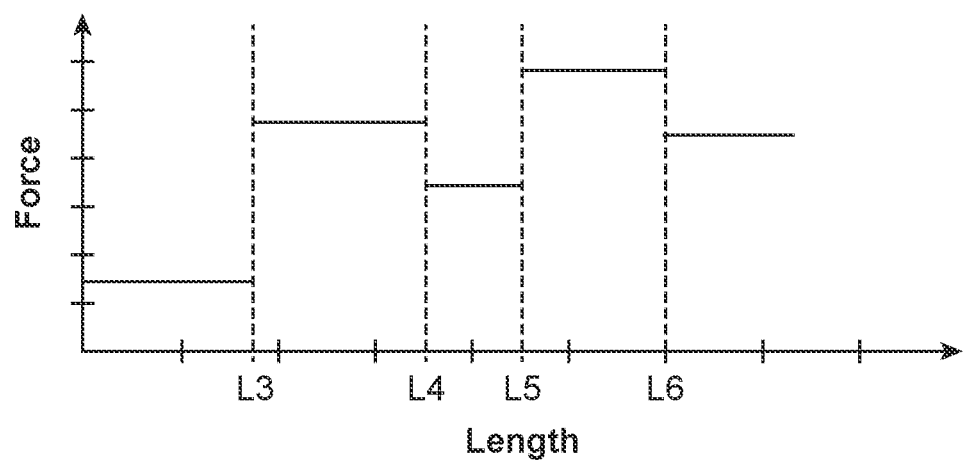

FIGS. 8A and 8B illustrate insertion force profiles associated with the cannula 520 and the cannula 620, respectively. As shown in FIG. 8A, the insertion force required to move a distal tip of an instrument, like the distal tip of the flexible shaft 506, varies along the length of the cannula 520, as described above in connection with FIGS. 7A-C. While the distal tip is located within the first portion 528a (associated with the length L1 and shown in FIG. 7A) the required force is at a first level. As the distal tip of the flexible shaft passes into the curved portion 528b (as shown in FIG. 7B), the level of force required increases. After the distal tip passes beyond the curved portion 528b (as shown in FIG. 7C), the level of force required to move at a constant velocity decreases. The level of force required for constant velocity after the distal tip passes beyond the curved portion 528b may be higher than the level of force required to move the distal tip along the first portion 528a. In some embodiments, the level of force required when the distal tip of the flexible shaft 506 is positioned within any given portion may be assigned into a category, such as low, medium, and high force levels.

FIG. 8B illustrates the insertion force profile associated with the cannula 620. Because the cannula 620 includes multiple curves, the insertion force profile associated with the cannula 620 may be more complicated than the insertion force profile of the cannula 520, as shown in FIG. 8A. As shown in FIG. 8B, the insertion force required to move the distal tip of the flexible shaft 506 along the channel 626 of the cannula 620 may be higher when the distal tip of the flexible shaft 506 is within the curved portions, portion 622b and portion 622d, defined between L3 and L4 and between L5 and L6, along the length axis. In general, the insertion force required to move the distal tip of a flexible shaft increases with the number of curved portions and the degree of curvature.

The insertion force profiles of FIGS. 8A and 8B are illustrated in simplified form, such that the force applied by the user to move the distal tip of the shaft of the flexible instrument at a constant velocity is generally constant within a given portion of the cannula. This is done for clarity in presenting insertion force profiles. In some implementations the insertion force profile may be represented by bands of force. For example, 0 to A along the x-axis of FIG. 8A may indicate a "low" insertion force is required; between A and B may indicate a "medium" level of insertion force is required; and forces higher than B may be considered to be a "high" insertion force. These levels or bands may then be used in determining appropriate damping force profiles for use in modulating a manually applied insertion force. More or fewer levels may be included in some insertion force profiles.

Figure 9:
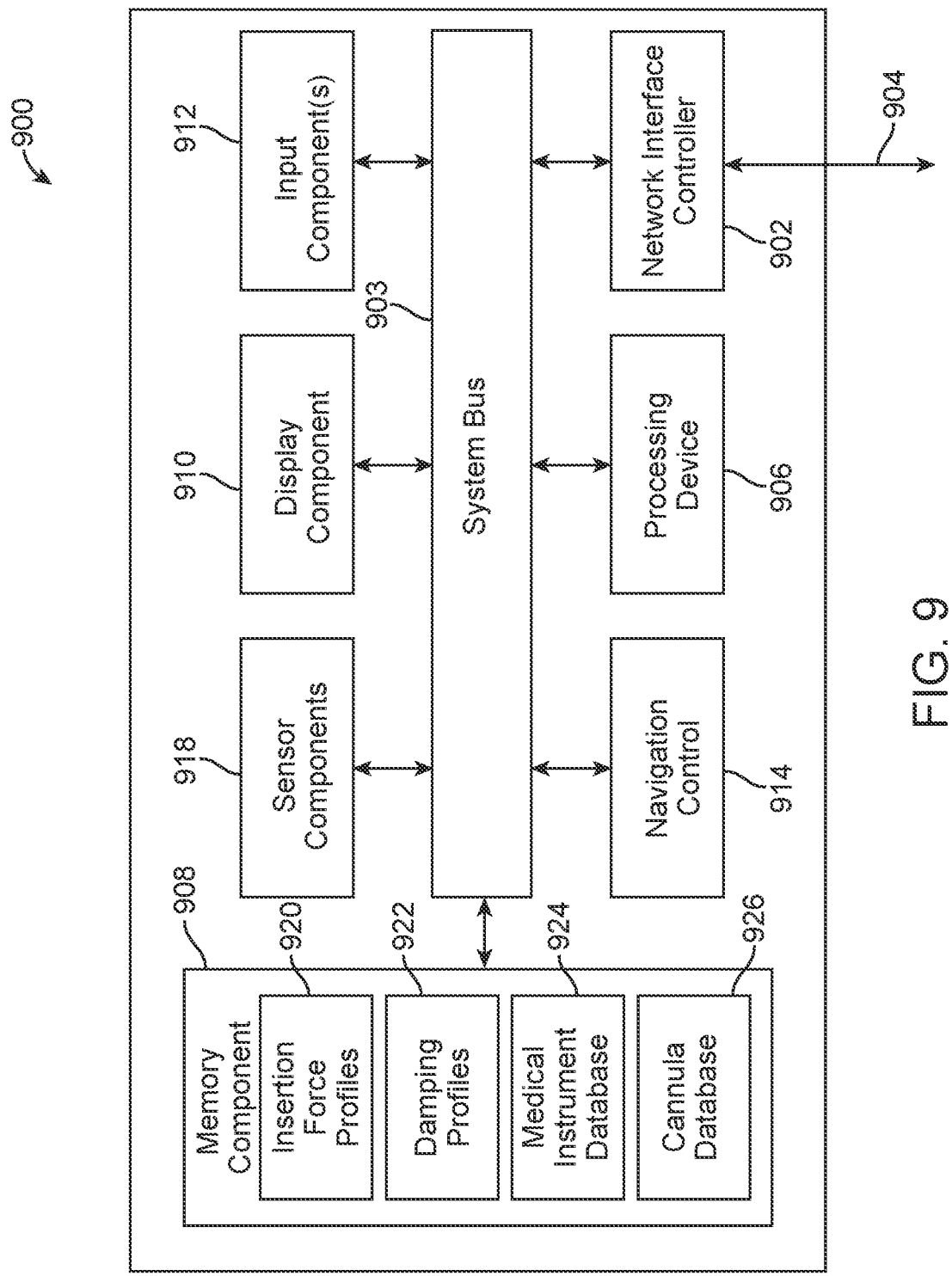
FIG. 9 is a diagram illustrating a computing device, consistent with some embodiments.

FIG. 9 is a diagram illustrating computing system 900, which may correspond to the control system 108 of FIG. 1, consistent with some embodiments. Components of the computing system 900 may be included in the master manipulator system 102 and/or the slave manipulator system 104. Further, the computing system 900 may also be a server or one server amongst a plurality of servers that are configured in communication via a network or communication link with the master manipulator system 102 and/or the slave manipulator system 104 to provide the control system 108. As shown in FIG. 9 computing system 900 includes a network interface controller (NIC) 902 configured for communication with a network via a network communication link 904, which may represent a wired or a wireless connection. Consistent with some embodiments, NIC 902 includes a wireless communication component, such as a wireless broadband component, a wireless satellite component, or various other types of wireless communication components including radio frequency (RF), microwave frequency (MWF), and/or infrared (IR) components configured for communication with other devices over a network. The NIC 902 may be capable of transmitting and receiving information according to one or more wireless network protocols, such as Wi Fi™, 3G, 4G, HDSPA, LTE, RF, NFC, IrDA, HomeRF, DECT, Wireless Telemetry, IEEE 802.11a, b, g, n, ac, or ad, Bluetooth®, BLE, WiMAX, ZigBee®, etc.

Consistent with some embodiments, computing system 900 includes a system bus 903 for interconnecting various components within computing system 900 and communicating information between the various components. Such components include a processing device 906, which may be one or more processors, micro-controllers, graphics processing units (GPUs) or digital signal processors (DSPs), and a data store or memory components 908, which may correspond to a random access memory (RAM), an internal memory component, a read only memory (ROM), or an external or static optical, magnetic, or solid-state memory. Consistent with some embodiments, computing system 900 further includes a display component 910 for displaying information to a user 101 of computing system 900. The display component 910 may be the stereoscopic image display system 136 of FIG. 3. Display component 910 may also be an additional display. Computing system 900 may also include an input component 912, allowing for a user of computing system 900, such as user 101, to input information to computing system 900. Such information could include instrument selections and instrument movement instructions. An input component 912 may include multiple components, for example, a keyboard or key pad, whether physical or virtual, a mouse, a touch screen, a microphone, an eye tracking system, and combinations thereof.

Computing system 900 may further include a navigation control component 914, configured to allow a user to direct motion of the manipulator arms 124a, 124b, 124c, and/or the instruments 128a, 128b, and 128c. Consistent with some embodiments, navigation control component 914 may be a mouse, a trackball, or other such device. The navigation control component 914 may be the master tool manipulators (MTM's) 132a and 132b of FIG. 3.

Computing system 900 may also include sensor components 918. Sensor components 918 provide sensor functionality, and may correspond to sensors built into the surgical system 100 or sensor peripherals coupled to control system 108. Sensor components 918 may include any sensory device that captures information related to the physical configuration and movement of the slave manipulator system 104 and the master manipulator system 102. Sensor components 918 may include camera and imaging components, accelerometers, linear encoders, angular encoders, biometric readers, motion capture devices, and other devices that are capable of providing information about the slave manipulator system 104.

Computing system 900 may perform specific operations by processing device 906 executing one or more sequences of instructions contained memory component 908. In other embodiments, hard-wired circuitry may be used in place of or in combination with software instructions to implement the present disclosure. Logic may be encoded in a computer-readable or machine-readable medium, which may refer to any medium that participates in providing instructions to processing device 906 for execution, including memory component 908. Consistent with some embodiments, the computer-readable medium is tangible and non-transitory.

As illustrated in FIG. 9, the memory component 908 may store insertion force profiles 920, like the insertion force profiles of FIGS. 8A and 8B. The memory component 908 may further store damping profiles 922, a medical instrument database 924, and a cannula database 926. The insertion force profiles 920 may be stored as arrays of numerical values that describe the insertion force relative insertion force required for movement of the distal tip of the flexible shaft of the instrument at a desired velocity. The memory component 908 may store many different insertion force profiles 920. For example, the insertion force profile of FIG. 8A may represent an insertion force profile associated with a specific medical instrument and a specific cannula. The insertion force profile of FIG. 8A may include this information for a specific desired velocity, such that a different desired velocity for the same medical instrument and cannula may have a unique insertion force profile.

The processing device 906 may receive an insertion force profile and calculate an array of damping coefficients to be applied by actuators included in the carriage 510 of FIGS. 5 and 6, according to movement of an instrument through a cannula and the velocity of movement.

Figure 10A:
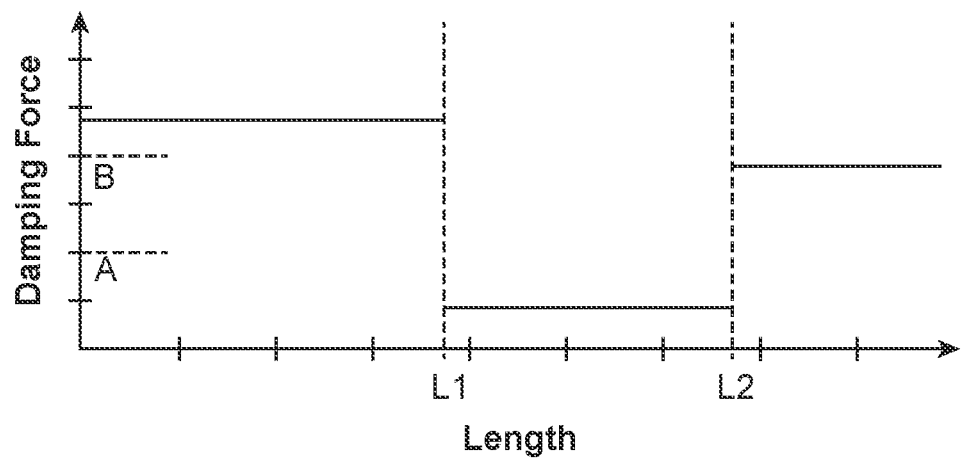
FIGS. 10A and 10B are plots relating a damping coefficient to a length along various cannula configurations.
Figure 10B:
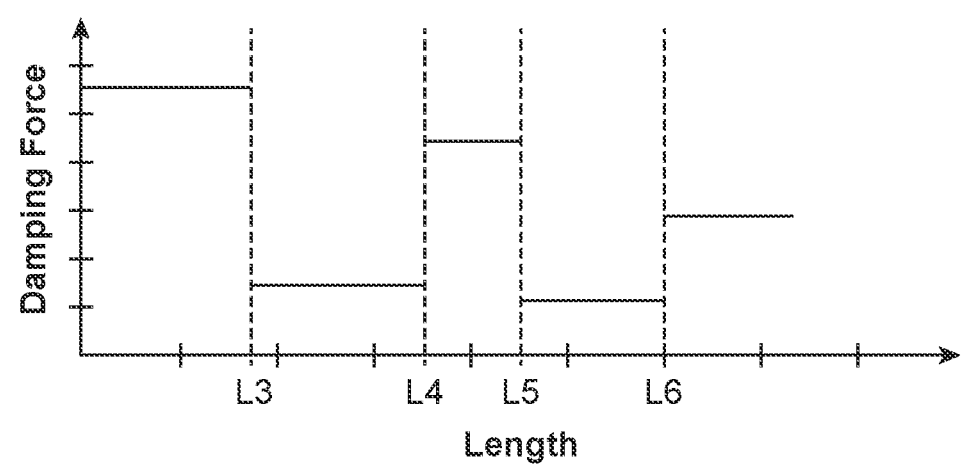

FIGS. 10A and 10B illustrate diagrams of exemplary damping coefficients that form damping coefficient profiles associated with cannulas 520 and 620, respectively. As illustrated in FIG. 10A, a higher damping coefficient may be applied while the distal tip of the flexible shaft 506 is within the first portion 528a of the cannula 520. The relatively lower damping coefficient may be applied when the distal tip of the flexible shaft 506 is within the second portion 528b of the cannula 520. The application of the higher damping coefficient when the force required to move at a given velocity is lower may effectively slow the progress of the distal tip of the flexible shaft 506 through the first portion 528a. When the force requirement goes up in the second portion 528b, due to the curvature of portion 528b, the damping coefficient applied should be lower. By applying higher damping coefficients when lower force is required and lower damping coefficients when higher forces required, the control system 108 may provide for a uniform velocity along the entire length of the cannula 520 and even extending beyond the cannula 520. Without the application of the damping coefficients, the change in force requirements caused by curves in the cannulas 520 and 620 may cause changes in the velocity during manual instrument introduction. In some embodiments, the damping coefficients may be bracketed or otherwise associated with category levels of damping force. A damping force or damping force coefficient below A along the x-axis may be considered or assigned to a "low" force category; between A and B may be assigned to a "medium" force category; and above B may be assigned to a "high" damping force category. Accordingly, some damping profiles may stores lengths and associated categories or levels. More or fewer damping force levels or associated damping force coefficients may be provided in other embodiments.

Figure 11:
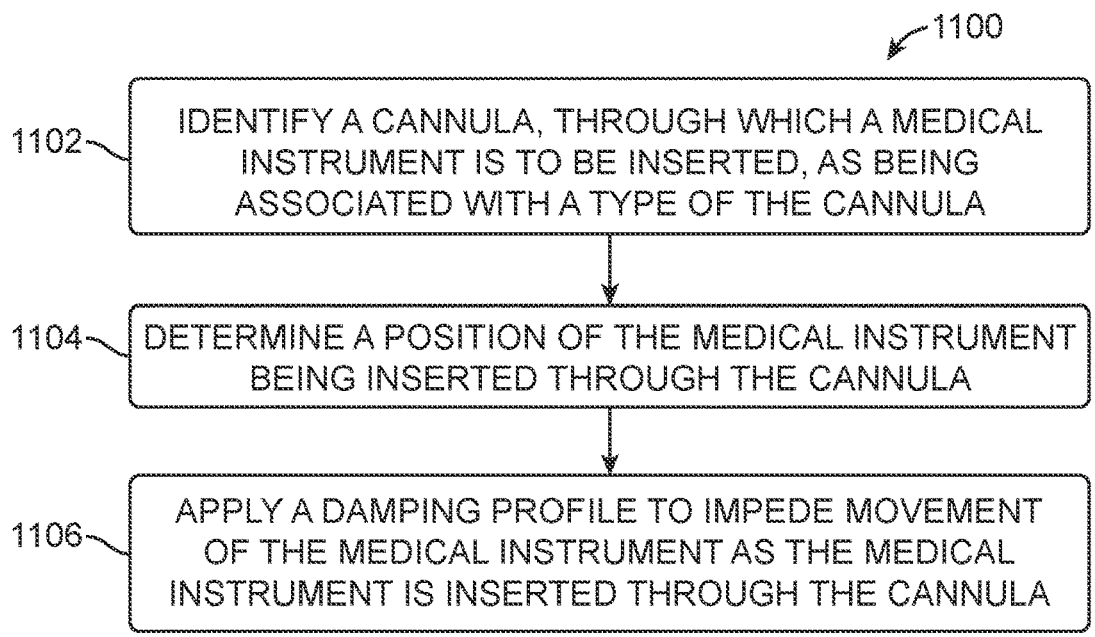
FIG. 11 is a flowchart of a method of controlling a teleoperational surgical system during insertion of a medical instrument through a cannula, consistent with some embodiments.

FIG. 11 is a flowchart of a method 1100 for controlling a teleoperational surgical system during insertion of a medical instrument through a cannula. The method 1100 is illustrated as a plurality of enumerated steps or operations. Additional operations may be performed before, after, in between, or as part of the enumerated operations. Additionally, some embodiments of the method 1100 may omit one or more of the enumerated operations. The operations of the method 1100 may be performed by the control system 108 of the surgical system 100 of FIG. 1.

As illustrated in FIG. 11, the method 1100 may begin at step 1102 in which a cannula is identified as being associated with a particular type of cannula. As an example, the control system 108 (FIG. 1) may identify the cannula 520 (FIG. 5) by reading a tag 532 disposed on the cannula 520. The tag 532 may include an identifier that is present in a cannula database 926 (FIG. 9). The cannula database 926 may include geometric information about the cannula 520, such as the length L1 of the first portion 528a and the length L2 of the second portion 528b. The geometric information may also include a curvature of the second portion 528b. In some embodiments, material information may also be included in the cannula database 926. Additionally, the tag 532 may be used to select an insertion force profile from the insertion force profiles 920 or a damping profile from the damping profiles 922 (FIG. 9).

At step 1104, a position of the medical instrument being inserted through the cannula may be determined. For example, the control system 108 may access one or more encoders associated with the manipulator 140 and the carriage 510 to determine a position of the carriage 510. By accessing information about the medical instrument in the medical instrument database 924, information such as a length of the medical instrument may be obtained from an instrument profile stored in the database 924. The position of the carriage 510 and the length of the medical instrument may be used by the control system 108 to determine a position or location of the distal tip of the medical instrument. Further, information from a cannula database 926 may also be used in determining the position of the distal tip of the medical instrument. In some embodiments, the medical instrument may include a tracking device at the distal tip or proximate to the distal tip of the flexible shaft of the medical instrument. For example, the distal tip of the medical instrument may include an electromagnetic tracker or other suitable device used to determine a location of the distal tip of the medical instrument in the surgical field.

At step 1106, one of a plurality of damping profiles is applied to resist the movement of the medical instrument as the medical instrument is inserted through the cannula. For example, a user may install a medical instrument and manually insert it through the cannula 520 by pushing it through at a certain velocity. The control system 108 may apply a damping profile having a plurality of damping coefficients associated with identifiable insertion lengths. Accordingly, the control system 108 may apply a lower damping coefficient during a curved portion of the cannula than a damping coefficient applied during a straight portion of the cannula as described herein. In this way, the control system 108 may modulate the insertion resistance (via the damping profile) to allow the user to move the medical instrument at a more consistent velocity through a cannula that requires different amounts of force at different positions within the cannula.

In some implementations, the damping profile with the plurality of damping coefficients may be calculated based on an insertion force profile. The insertion force profile may be associated with a specific cannula and a specific medical instrument. The insertion force profile may be obtained from a memory component, like the memory component 908 of FIG. 9, after the medical instrument is properly connected to a slave manipulator system 104 and after a cannula has been identified to the control system 108.

Figure 12:
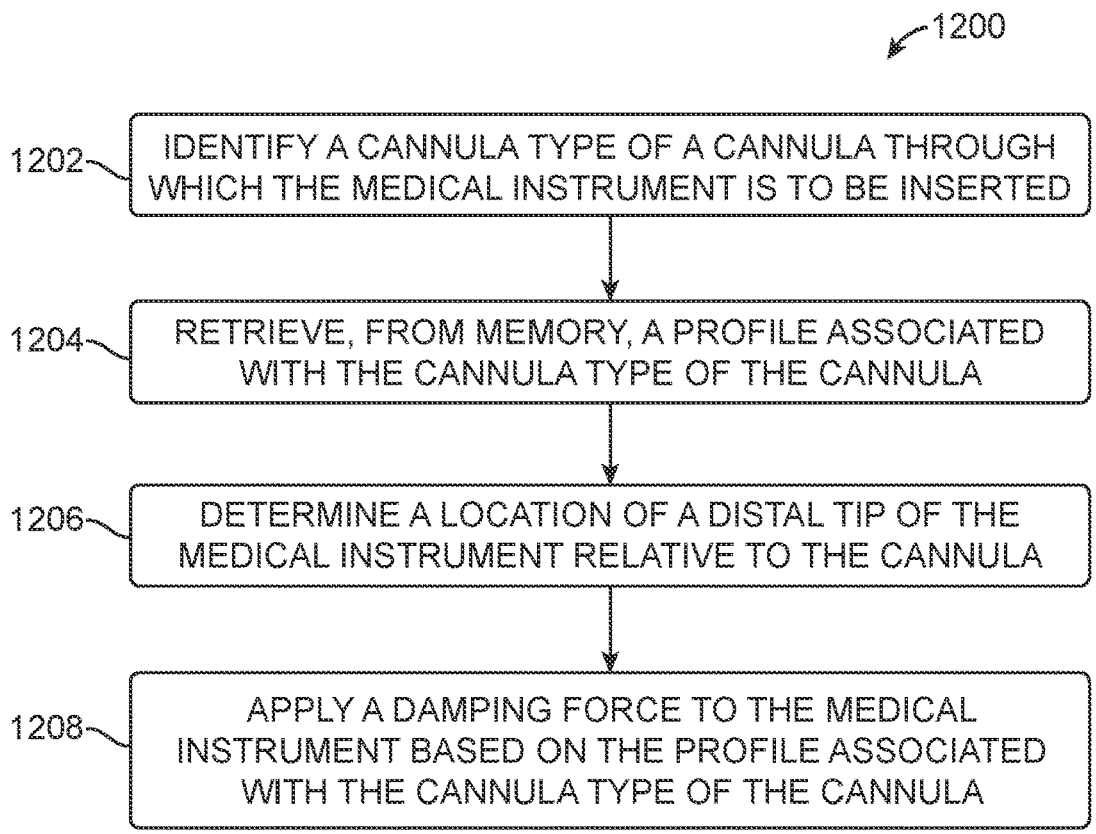
FIG. 12 is a flowchart of another method of controlling a teleoperational surgical system during insertion of a medical instrument through a cannula, consistent with some embodiments.

FIG. 12 is a flowchart of a method 1200 for controlling a teleoperational surgical system during insertion of a medical instrument through a cannula. The method 1200 is illustrated as a plurality of enumerated steps or operations, and may include other operations before, after, in between, or as part of the enumerated operations. The operations of the method 1100 may be performed by the control system 108 of the surgical system 100 of FIG. 1.

Embodiments of the method 1200 may begin at step 1202, in which a cannula type of a cannula through which a medical instrument is to be inserted is identified. The identification may include querying a cannula database 926 stored in a memory component 908 of a computing system 900 (FIG. 9). At step 1204, a profile associated with the cannula& may be retrieved from memory. For example, using type of the cannula or an identifier obtained from the cannula database 926, an insertion force profile may be obtained from the insertion force profiles 920 and/or a damping profile may be obtained from the damping profiles 922.

At step 1206, the location of the distal tip of the medical device being inserted through the cannula may be determined. The location may be determined relative to the cannula itself. For example, the control system 108 may determine that a distal tip of the flexible shaft 506 of the medical instrument 502 is positioned within a portion 622*c* of the cannula 620. By reference to the retrieved damping profile or the retrieved insertion force profile, a damping force coefficients associated with the portion 622*c* of the cannula 620 may be determined. For example, the damping force coefficient may be included in an array of damping force coefficients, where each value in the array is associated with a particular location along or portion of the cannula 620.

At step 1208, the damping coefficient may be applied to provide the damping force for the current insertion velocity. The insertion velocity may be determined by the control system 108 based on the differentiation of the position of the carriage 510 over a period of time. The application of the damping coefficient may cause a decrease in the insertion velocity along one of these straight portions 622*a* and 622*c*. Because the insertion velocity of the medical instrument may naturally decrease within the curved portions 622*b* and 622*d*, the damping coefficient may cause no decrease or a small decrease in the insertion velocity. Because the application and magnitude of the damping coefficient may change with position along a cannula the insertion velocity may be made more uniform, which may reduce the likelihood of damaging the cannula interior wall as well as causing instrument buckling when instrument transition from a straight portion to a curved portion such as from 622*a* to 622*b*.

Embodiments of the method 1200 may further include a step of monitoring the insertion velocity of the medical instrument. Applying the damping coefficient to the insertion velocity of the medical instrument may determine whether an insertion velocity of the medical instrument exceeds a threshold velocity. For example, a low insertion velocity may be more easily consistently maintained regardless of the curves of the cannula. In such instances, application of the damping coefficient may slow the procedure without providing significant benefits to the user. The threshold velocity may depend on the cannula and the medical instrument being inserted through the cannula. For example, a different threshold velocity may be applied to the first portion 528*a* of the cannula 520 then the threshold velocity applied to the second portion 528*b* of the cannula 520. Additionally, applying the damping coefficient to the insertion velocity of the medical instrument may include applying a first damping coefficient associated with a first portion of the cannula type and then applying a second damping coefficient associated with a second portion of the cannula type, as the medical instrument passes through the cannula.

Figure 13:
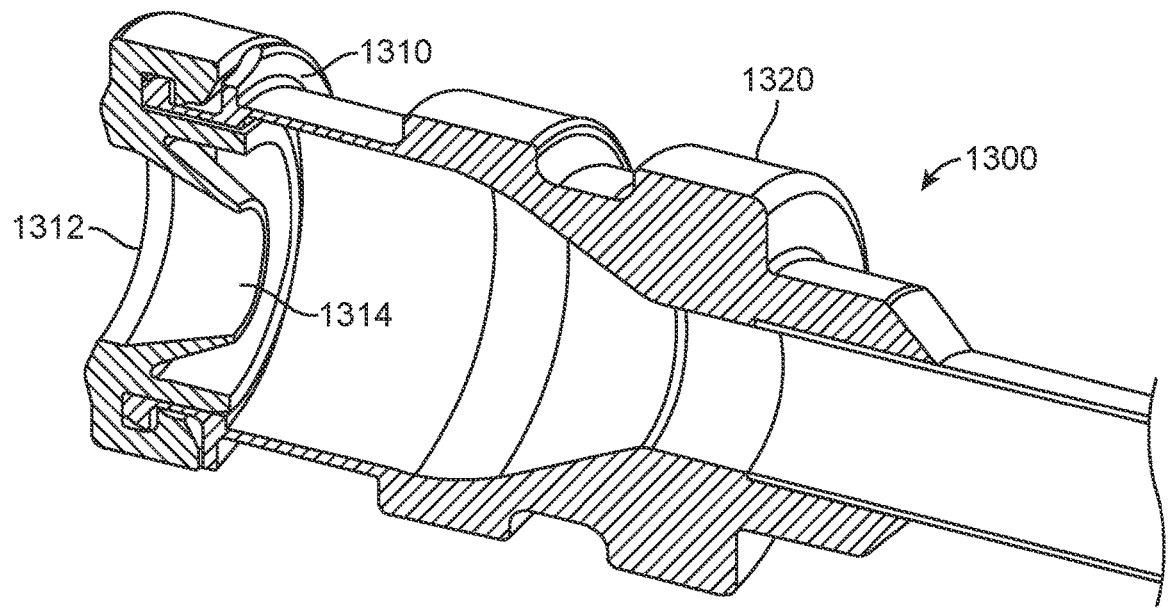
FIG. 13 is a plan view of an example cannula assembly, consistent with some embodiments.

Much of the previous discussion is in association with flexible medical instruments and curved cannulas. However, the techniques described can also be used with rigid medical instruments, straight cannulas, other cannula components, etc. FIG. 13 shows an example cannula assembly 1300, consistent with embodiments. Cannula assembly 1300 comprises two cannula components: a straight cannula 1320 and a cannula seal 1310. The cannula seal 1310 includes a proximal opening 1312 and a distal opening 1314 that is smaller in diameter than the proximal opening 1312. During a medical procedure, a medical instrument (such as surgical instrument 502 or a rigid surgical instrument) may be inserted through the cannula seal 1310. As the instrument is inserted through and interacts with the seal, different resistive forces may be provided by the cannula seal. The techniques described above can also be used to increase the uniformity of the manual insertion force required as the instrument is inserted through the seal. For example, the techniques described above can be used to reduce the change in the manual insertion force required as more of the instrument is inserted through the seal 1310 and into the cannula assembly 1300. The increase in uniformity, or the reduction in the change in the manual insertion force required may be sufficient to meet any appropriate criterion. Some example criteria include: the resulting variation in manual insertion force required is not noticed by an average human operator, is not sufficient to cause an average human operator to mis-insert the medical instrument, is within 10%, or any other appropriate criterion.

Figure 14:
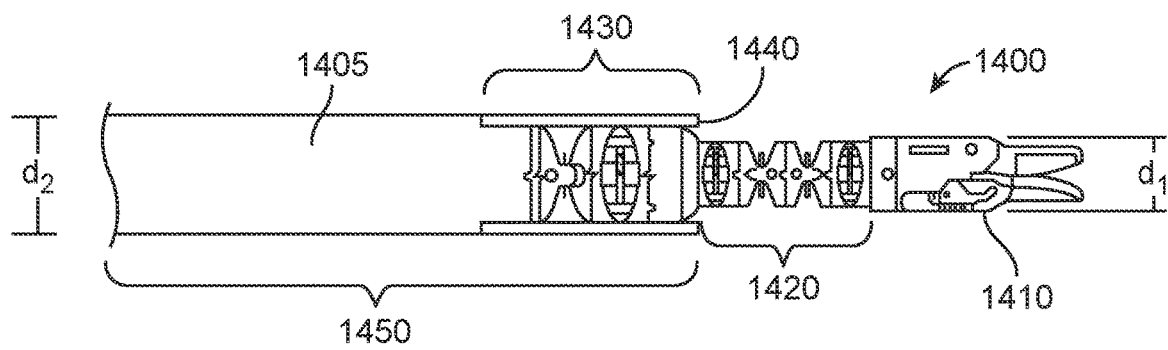
FIG. 14 shows part of an example medical instrument 1400, consistent with some embodiments.

FIG. 14 shows part of an example medical instrument 1400, consistent with embodiments. The medical instrument 1400 comprises a shaft 1405 connected to an end effector 1410 via a wrist 1420. Although the geometries of the end effector 1410 and the wrist 1420 differ, the end effector 1410 and the wrist 1420 have about the same diameter $d_1$. The instrument 1400 also comprises a first portion 1430 covered by a sheath 1440, and a second portion 1450. Sheath 1440 is shown in cross section so the parts of medical instrument 1400 that would be obscured by sheath 1440 is visible in FIG. 14. The first portion 1430 and the second portion 1450 have different diameters, but the sheath 1440 increases the diameter of the instrument at the first portion 1430 such that it is the same as the diameter $d_2$ of the second portion 1450. The diameter $d_2$ is greater than the diameter $d_1$. Thus, as the instrument 1400 is inserted a cannula assembly (such as cannula assembly 1300) and traverses the cannula seal 1310, the instrument 1400 deflects the distal opening 1314 by different amounts and contacts the distal opening 1314 with different materials. Specifically, when the part of the instrument 1400 having diameter $d_2$ contacts and moves against the distal opening 1314, it deforms the cannula seal 1310 more than would the part of the instrument 1400 having diameter $d_1$. The greater deformation of the cannula seal 1310 due to the part of the instrument 1400 having diameter $d_2$ results in greater contact forces from deformation between the instrument 1400 and the cannula seal 1310. These greater contact forces can increase the resistive force provided by the cannula seal 1310 against the insertion of the instrument 1400 through the cannula assembly 1300. Even when a part of the instrument 1400 having the same diameter (e.g. first portion 1430 with sheath 1440, and second portion 1450, with diameter $d_2$) is inserted through the cannula seal 1310 at an unchanging speed, the resulting resistive force from the cannula seal 1310 may change. For example, sheath 1440 may have a first friction response to the cannula seal 1310, and the second portion 1450 may have a second friction response to the cannula seal 1310 different from the first friction response. Thus, a frictional component of the resistive force provided by the cannula seal 1310 to the insertion of the instrument 1400 can change.

The techniques described herein can be used to provide a control system (such as control system 108) communicatively coupled with the manipulator supporting the instrument 1400. This control system may be operative to determine an insertion profile associated with at least one of the instrument 1400 and the cannula seal 1310, and control an insertion force in accordance with the insertion profile and affect motion of the instrument 1400 during manual insertion of the medical instrument through the cannula seal 1310. The control of the insertion force may be used to account for differences in diameter, material, and other force affecting characteristics of the instrument 1400, the cannula seal 1310, or both.

Embodiments of the present systems and methods may provide for a more uniform insertion force or velocity when inserting a medical instrument through a cannula component, such as a flexible instrument through a curved cannula with one or more curved portions. The systems and methods may compensate for differences in the insertion force required.

In some embodiments, a teleoperational surgical system comprises a manipulator and a control system. The manipulator is configured to be operatively coupled to a medical instrument. The manipulator is adapted to move the medical instrument through a cannula component. The control system is communicatively coupled with the manipulator. The control system is operative to determine an insertion profile associated with at least one of the medical instrument and the cannula component. The control system is configured to control an insertion force in accordance with the insertion profile and affect motion of the medical instrument during manual insertion of the medical instrument through the cannula component.

In some embodiments of this teleoperational surgical system, the insertion profile comprises a first part configured to assist the motion of the medical instrument during the manual insertion of the medical instrument through the cannula component and a second part configured to impede the motion of the medical instrument during the manual insertion of the medical instrument through the cannula component.

In some embodiments of this teleoperational surgical system, the medical instrument comprises a proximal end, a distal end, and a flexible portion between the proximal and distal ends, the cannula component is a curved cannula, the manual insertion of the medical instrument through the cannula component comprises manual movement of the distal end and at least part of the flexible portion into the curved cannula, and the insertion profile is configured to increase a spatial uniformity of a manual insertion force to be exerted to manually insert the medical instrument through the cannula component.

In some embodiments of this teleoperational surgical system, the medical instrument comprises a shaft having first and second shaft portions configured to be manually inserted through the cannula component. The first shaft portion having a first friction response to the cannula component and the second shaft portion having a second friction response to the cannula component different from the first friction response. The insertion profile is configured to increase a spatial uniformity of a manual insertion force as the first and second shaft portions are manually inserted through the cannula component.

In some embodiments of this teleoperational surgical system, The cannula component comprises a cannula seal. The control system is operative to determine the insertion profile associated with at least one of the medical instrument and the cannula component by determining the insertion profile associated with the medical instrument, the insertion profile based on a diameter of the medical instrument.

In some embodiments of this teleoperational surgical system, the medical instrument is a flexible medical instrument including a proximal end, a distal end, and a flexible portion between the proximal and distal ends, the cannula component is a curved cannula, and the insertion profile is a damping profile configured to impede the motion of the medical instrument during the manual insertion of the flexible medical instrument through the curved cannula. The control system may be operative to determine the insertion profile associated with the at least one of the medical instrument and the cannula component by: identifying the cannula component (or the medical instrument, or the cannula component and the medical instrument), and determining the insertion profile associated with at least the cannula component, (or with at least the medical instrument, or with both the cannula component and the medical instrument).

In some embodiments, a method of controlling a teleoperational surgical system is used during insertion of a medical instrument through a cannula component. The method comprises identifying at least one element type and retrieving an insertion profile from memory. The element type is an instrument type of the medical instrument, or a cannula component type of the cannula component. The insertion profile is associated with the at least one component type. The method further comprises determining a location of the medical instrument relative to the cannula component, and applying an impeding or assistive force to the medical instrument based on the insertion profile as the medical instrument is inserted through the cannula component.

In some embodiments of this method, the insertion profile comprises a first part configured to assist motion of the medical instrument during manual insertion through the cannula component, and a second part configured to impede motion of the medical instrument during manual insertion through the cannula component.

In some embodiments of this method, determining the location of the medical instrument relative to the cannula component comprises determining a location of a distal tip of the medical instrument relative to the cannula component. The at least one element type comprises the cannula component type. The medical instrument is a flexible medical instrument including a proximal end, a distal end, and a flexible portion between the proximal and distal ends. The cannula component is a curved cannula. The insertion profile is associated with at least the cannula component type and is a damping profile configured to impede motion of the medical instrument as the medical instrument is inserted through the cannula component.

In various embodiments of this method, the at least one element type comprises the cannula component type, comprises the instrument type, or comprises both the instrument type and the cannula component type.

One or more elements in embodiments of the invention may be implemented in software to execute on a processor of a computer system such as control system 108. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A manipulator system comprising:
   a manipulator configured to support an instrument; and
   a control system coupled to the manipulator;
   wherein the control system is configured to:
   determine an insertion force profile, the insertion force profile being based on at least one type selected from the group consisting of: a type of the instrument and a type of a cannula through which the instrument is configured to be inserted, and
   resist or assist a manual insertion of the instrument through the cannula according to the insertion force profile, wherein the resisting or assisting causes a velocity of the manual insertion to be uniform in response to a uniform force applied by the manual insertion.

2. The manipulator system of claim 1, wherein to resist or assist the manual insertion, the control system is configured to apply, using the manipulator, a resistive force or an assistive force to the instrument.

3. The manipulator system of claim 1, wherein to resist or assist the manual insertion, the control system is configured to apply a resistive force or an assistive force to a carriage of the manipulator to which the instrument is mounted.

4. The manipulator system of claim 1, wherein the insertion force profile comprises:
   a first part configured to assist the manual insertion of the instrument; and
   a second part configured to resist the manual insertion of the instrument.

5. The manipulator system of claim 1, wherein the insertion force profile comprises a plurality of damping levels associated with locations along the cannula.

6. The manipulator system of claim 1, wherein the control system is further configured to determine the insertion force profile based on a desired velocity for the manual insertion.

7. The manipulator system of claim 1, wherein the insertion force profile defines an amount to resist or assist the manual insertion based on a position of the instrument within the cannula.

8. The manipulator system of claim 1, wherein:
   the instrument comprises a proximal end, a distal end, and a flexible portion between the proximal end and the distal end;
   the cannula comprises a curved portion; and
   the manual insertion of the instrument through the cannula comprises manual movement of the distal end and at least part of the flexible portion into the curved portion of the cannula.

9. The manipulator system of claim 1, wherein to determine the insertion force profile, the control system is configured to:
   identify the type of the cannula, the type of the instrument, or both the type of the cannula and the type of the instrument; and
   determine the insertion force profile based on the type of the cannula, the type of the instrument, or both the type of the cannula and the type of the instrument.

10. The manipulator system of claim 9, wherein to identify the type of the cannula, the control system is configured to:
   sense a magnetic binary pattern of the cannula; or
   read a radio-frequency identification tag (RFID) of the cannula; or
   read a visible tag located on the cannula.

11. The manipulator system of claim 1, wherein the control system is further configured to:
   monitor a velocity of the instrument through the cannula; and
   determine an amount to resist or assist the manual insertion based on the insertion force profile and the monitored velocity.

12. A method of controlling a manipulator system comprising a manipulator configured to support an instrument, the method comprising:
   determining, by a control system of the manipulator system, an insertion force profile, the insertion force profile being based on at least one type selected from the group consisting of: a type of the instrument and a type of a cannula through which the instrument is configured to be inserted; and
   commanding, by the control system, the manipulator to resist or assist, by the control system, a manual insertion of the instrument through the cannula according to the insertion force profile, wherein the resisting or assisting causes a velocity of the manual insertion to be uniform in response to a uniform force applied by the manual insertion.

13. The method of claim 12, wherein commanding the manipulator to resist or assist the manual insertion comprises:
   commanding the manipulator to apply a resistive force or an assistive force to the instrument; or
   commanding a resistive force or an assistive force to be applied to a carriage of the manipulator, wherein the instrument is mounted to the carriage.

14. The method of claim 12, further comprising determining, by the control system, the insertion force profile based on a desired velocity for the manual insertion.

15. The method of claim 12, wherein the insertion force profile defines an amount to resist or assist the manual insertion based on a position of the instrument within the cannula.

16. The method of claim 12, wherein determining the insertion force profile comprises:
   identifying, by the control system, the type of the cannula, the type of the instrument, or both the type of the cannula and the type of the instrument; and
   determining, by the control system, the insertion force profile based on the type of the cannula, the type of the instrument, or both the type of the cannula and the type of the instrument.

17. The method of claim 12, further comprising:
   monitoring, by the control system, a velocity of the instrument through the cannula; and
   determining, by the control system, an amount to resist or assist the manual insertion based on the insertion force profile and the monitored velocity.

18. The method of claim 12, wherein the method further comprises:
   monitoring a velocity of the instrument through the cannula; and
   determining an amount to resist or assist the manual insertion based on the insertion force profile and the monitored velocity.

19. A non-transitory computer-readable medium storing instructions for controlling operation of one or more processors of a system configured to support an instrument, the instructions, when executed by the one or more processors, cause the one or more processors to perform a method comprising:
   determining an insertion force profile, the insertion force profile being based on at least one type selected from the group consisting of: a type of the instrument a type of a cannula through which the instrument is configured to be inserted; and
   command a resisting or an assisting of a manual insertion of the instrument through the cannula according to the insertion force profile, wherein the resisting or assisting causes a velocity of the manual insertion to be uniform in response to a uniform force applied by the manual insertion.

20. The non-transitory computer-readable medium of claim 19, wherein commanding the resisting or the assisting of the manual insertion comprises:
   commanding an application of a resistive force or an assistive force to the instrument; or
   commanding an application of a resistive force or an assistive force to a carriage of a manipulator to which the instrument is mounted.

* * * * *

UNITED STATES PATENT AND TRADEMARK OFFICE
CERTIFICATE OF CORRECTION

PATENT NO.       : 12,097,001 B2
APPLICATION NO.  : 17/236874
DATED            : September 24, 2024
INVENTOR(S)      : Melody Wu and Samuel Kwok Wai Au Page 1 of 1

It is certified that error appears in the above-identified patent and that said Letters Patent is hereby corrected as shown below:

On the Title Page

(63) Related U.S. Application Data:
Please delete "Continuation of application No. 16/084,449, filed as application No. PCT/US2017/018193 on Feb. 16, 2017, now Pat. No. 11,013,567." and insert --Continuation of application No. 16/084,449, filed on Sep. 12, 2018, now Pat. No. 11,013,567, which is a 371 of application No. PCT/US2017/018193, filed on Feb. 16, 2017.--;

In the Claims

Column 22, Claim 19, Line 34:
Please insert --and-- after instrument.

Signed and Sealed this
Second Day of September, 2025

Coke Morgan Stewart
*Acting Director of the United States Patent and Trademark Office*